US006072093A

United States Patent [19]

O'Neill et al.

[11] Patent Number: 6,072,093

[45] **Date of Patent: *Jun. 6, 2000**

[54] PROCESS FOR OLIGOMER PRODUCTION AND SATURATION

[75] Inventors: Patrick S. O'Neill, Williamsville, N.Y.; Laurence O. Stine, Western Springs, Ill.; Brian S. Muldoon, Mt. Prospect, Ill.; Steven C. Gimre, Carol Stream, Ill.; Robert R. Frame, Glenview, Ill.

[73] Assignee: UOP LLC, Des Plaines, Ill.

[ * ] Notice: This patent is subject to a terminal disclaimer.

[21] Appl. No.: 09/187,714

[22] Filed: Nov. 6, 1998

Related U.S. Application Data

[63] Continuation-in-part of application No. 08/990,828, Dec. 15, 1997, Pat. No. 5,895,830, which is a continuation-in-part of application No. 08/573,314, Dec. 15, 1995.

[51] Int. Cl.$^7$ .......... C07C 2/08; C07C 2/18

[52] U.S. Cl. .......... 585/514; 585/326; 585/329

[58] Field of Search .......... 585/502, 509, 585/513, 514, 326, 329, 332

[56] References Cited

U.S. PATENT DOCUMENTS

| | | | |
|---|---|---|---|
| 2,526,966 | 10/1950 | Oberfell et al. | 196/1 |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,200,714 | 4/1980 | Mahoney et al. | 526/68 |
| 4,254,294 | 3/1981 | Juguin et al. | 585/525 |
| 4,304,948 | 12/1981 | Vora et al. | 585/315 |
| 4,393,259 | 7/1983 | Ward et al. | 585/315 |
| 4,456,781 | 6/1984 | Marsh et al. | 585/533 |
| 4,463,211 | 7/1984 | Manning | 585/510 |
| 4,678,645 | 7/1987 | Chang et al. | 422/190 |
| 4,749,820 | 6/1988 | Kuo et al. | 585/330 |
| 4,830,635 | 5/1989 | Harandi et al. | 44/56 |
| 4,853,015 | 8/1989 | Herbst et al. | 207/74 |
| 5,049,360 | 9/1991 | Harandi et al. | 422/141 |
| 5,134,242 | 7/1992 | Le et al. | 585/533 |
| 5,811,608 | 9/1998 | Stine et al. | 585/316 |
| 5,811,617 | 9/1998 | Shubkin et al. | 585/511 |

FOREIGN PATENT DOCUMENTS

| | | |
|---|---|---|
| 2186287 | 2/1987 | United Kingdom . |

*Primary Examiner*—Bekir L. Yildirim
*Attorney, Agent, or Firm*—Thomas K. McBride; John G. Tolomei

[57] ABSTRACT

A process for the production of $C_8$ and higher olefins by the oligomerization of light olefins to heavier olefins is improved by the addition of cycloparaffins to the oligomerization zone. The recycle of the cycloparaffins extends the catalyst activity and improves the catalyst life. Cyclohexane provides an excellent solvent for removing deposits from the catalyst with chemical inertness to the process and a boiling range that allows its essentially complete recovery when producing nonenes and higher olefins from propylene feeds.

20 Claims, 1 Drawing Sheet

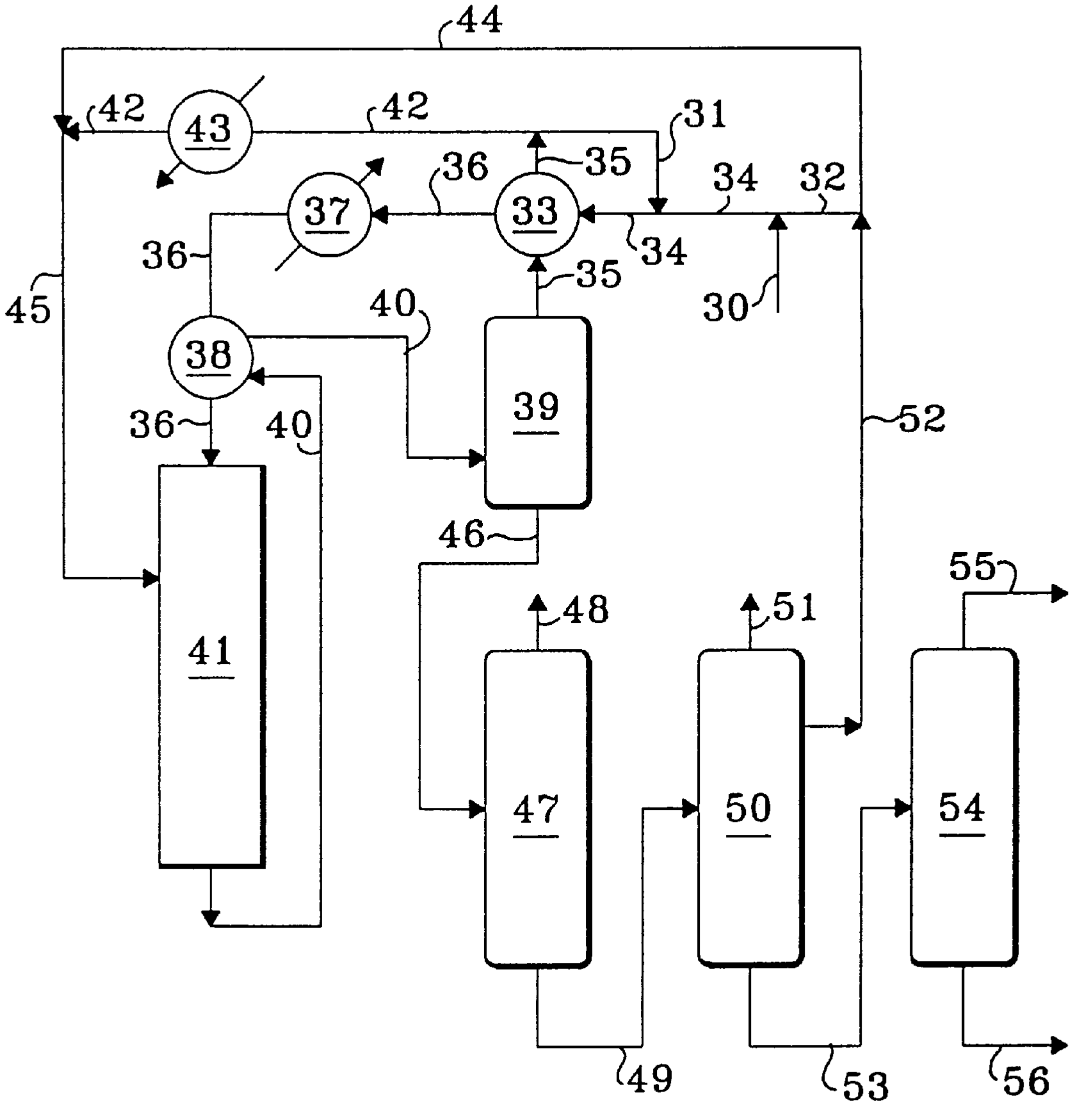
44
42
43
42
31
35
36
37
33
34
32
34
36
45
35
30
40
38
39
52
36
40
46
41
55
48
51
47
50
54
49
53
56

PROCESS FOR OLIGOMER PRODUCTION AND SATURATION

CROSS REFERENCE TO RELATED APPLICATION

This application is a continuation in part of application Ser. No. 08/990,828 filed Dec. 15, 1997, now U.S. Pat. No. 5,895,830 the contents of which are hereby incorporated by reference, which is a continuation in part of Ser. No. 08/573,314, filed Dec. 15, 1995, now abandoned, the contents of which are hereby incorporated by reference.

FIELD OF THE INVENTION

This invention relates generally to the production of oligomers from light olefins.

BACKGROUND OF THE INVENTION

Prior Art

Processes for the oligomerization of light olefins to produce $C_7$ and higher carbon number oligomers are well known. Oligomerization processes have been long employed to produce good quality motor fuel components from propylene and butylene. Such oligomerization processes are also referred to as catalytic condensation and polymerization with the resulting motor fuel often referred to as polymer gasoline. Methods have always been sought to improve the octane number of the gasoline boiling range oligomerization products. In addition the oligomerization process is also susceptible to catalyst fouling from the condensation of heavy oligomers into coke that covers the catalyst.

Another process that has met the continuing demand for the conversion of light hydrocarbons into high octane motor fuels was the alkylation of isobutane with propylene, butenes and amylenes using a hydrofluoric acid (HF) catalyst, commonly referred to as HF alkylation. The HF process has provided a highly successful method for the production of high octane motor fuels. Despite a long history of safe operation, recent concerns over the possibility of a catastrophic release of HF acid from HF alkylation units has prompted the investigation of modification or alternatives to the HF alkylation process for the production of motor fuels. One existing alternative is a similar alkylation process that uses sulfuric acid as the catalyst. While the use of sulfuric acid may decrease the degree of the hazard that some associate with the use of HF acid, the sulfuric acid process is still perceived as possibly presenting the same hazard and is not as economically advantageous as the HF alkylation process. Therefore, processing methods have been sought to improve the operation of oligomerization processes as substitutes for acid catalyzed alkylation.

A number of arrangements are known for using oligomerization in combination with other processes such as saturation and dehydrogenation as substitutes for acid catalyzed isomerization alkylation. Patents disclosing the dehydrogenation of light paraffin stream with oligomerization of the dehydrogenation effluent include U.S. Pat. No. 4,393,259, U.S. Pat. No. 5,049,360, U.S. Pat. No. 4,749,820, U.S. Pat. No. 4,304,948 and U.S. Pat. No. 2,526,966.

It also known to hydrotreat the olefinic hydrocarbon streams produced by oligomerization to saturate olefins. Patent GB 2186287 discloses dehydrogenation of and oligomerization of a C4 fraction to produce a jet aircraft fuel that is optionally hydrogenated into premium gasoline. The hydrotreatment of jet fuels, diesel fuels and lubes produced by dehydrogenation and oligomerization of light paraffins is disclosed in U.S. Pat. No. 4,678,645. However, hydrotreating is not always beneficial for gasoline fractions produced by oligomerization and can lower octane ratings, but is known to be particularly beneficial when saturating isooctenes to isooctanes.

Some prior art process that use highly acidic halide type catalysts for polymerization have suggested the recycle of paraffins to the polymerization zone for purposes of cooling. Such references include U.S. Pat. No. 4,200,714 and U.S. Pat. No. 4,254,294.

In processes for the production of heavy oligomers there are often high purity requirements. For example trimer and tertramers typically have purity requirements of 98% or more. Therefore the loss of any circulating streams to the product must be kept at minimal levels.

It is an object of this invention to improve the operation of an oligomerization reaction zone by extending the catalyst life.

It is a yet further object of this invention to reduce the impact of catalyst fouling by coke accumulation in oligomerization processes.

A further object of this invention is to facilitate the recovery of heavy hydrocarbons for recirculation in an oligomerization process.

BRIEF SUMMARY OF THE INVENTION

It has been surprisingly found that the introduction of cycloparaffins into an oligomerization zone for the oligomerization of light olefins will reduce catalyst fouling and significantly improve the operation of the oligomerization zone by facilitating recovery of a cycloparaffin recycle stream from the product. The process introduces a stream of cycloparaffins, typically in the $C_5$ to $C_7$ range, into the oligomerization zone. The cycloparaffins keep the surface of the catalyst flushed of heavy isomers that can condense and foul the surface of the catalyst. In addition to the inhibition of fouling, the recycling of the heavy paraffins to the oligomerization zone maintains the activity of the catalyst that promotes the selectivity of the oligomerization zone to desired olefins. The cycloparaffins, particularly cyclohexane, are readily recovered from lower boiling feed hydrocarbons and higher boiling products. In addition the stability of the saturated ring structure gives the cycloparaffins greater non-reactivity over the corresponding linear and branched paraffins.

While not wishing to be bound to any theory it is believed that the flushing action of the cycloparaffins may be responsible for the improved selectivity of the oligomerization products. Flushing of the catalyst with the cycloparaffin stream increases the liquid phase flow across the catalyst. The liquid phase flow may be responsible for rapidly removing the initial products from the surface of the catalyst before further reaction can take place to form heavies and cracked products. The oligomerization reaction is highly exothermic so it is believed that the presence of the liquid paraffin also moderates any temperature rise in the reaction zone overall and locally within the catalyst beds.

A number of specific operational steps can separately or collectively provide the oligomerization improvements of this invention. The flushing benefits of this invention are facilitated by the use of liquid phase conditions and the cycloparaffins. Passing heavier cycloparaffins, such as cyclohexane further enhances the improvements of this invention to the oligomerization zone. Cyclohexane is an excellent solvent and in most cases will readily remove typical deposits that foul the catalyst. The benefit of cyclohexane as a solvent should again surpass those of the heavier branched and linear paraffins. Substantial liquid phase conditions in conjunction with the heavy paraffin addition of this invention will offer substantial improvements to the catalyst life, and the catalyst life may be further improved as the oligomerization zone approaches 100% liquid phase conditions. In the production of motor fuel it has also been discovered that the heavy liquid recycle can raise octane number of gasoline streams substantially when used in conjunction with a mild acid catalyst in the oligomerization zone.

Accordingly in one embodiment this invention is an oligomerization process for the production of $C_8$ and higher carbon number olefins. The process comprises passing an oligomerization zone feed comprising $C_3$ and/or higher carbon number olefins to an oligomerization zone and contacting the oligomerization zone feed at oligomerization conditions with an oligomerization catalyst. A saturate stream comprising cycloparaffins having a carbon number of at least 5 passes into contact with the feed and the catalyst. The process recovers an oligomerization effluent stream comprising the paraffins and product oligomers having 8 or more carbon atoms.

In another embodiment this invention is a process for the production of $C_9$ and higher carbon number oligomers. The process comprises passing an oligomerization zone feed comprising $C_3$ and/or $C_4$ olefins to an oligomerization zone and contacting the oligomerization zone feed at oligomerization conditions with a solid phosphoric acid catalyst. A cyclohexane containing stream passes into contact with the feed and the catalyst in the oligomerization zone to maintain at least a portion of the combined cyclohexane stream and feed in liquid phase conditions in the oligomerization zone. An oligomerization effluent stream comprising the cyclohexane and product oligomers comprising $C_9$ and higher olefin products is recovered. Separation of the oligomerization effluent stream produces an oligomerization product stream comprising product oligomers and recovers at least a portion of said cyclohexane for recycle.

Other objects, embodiments and details of this invention will be provided in the following detailed disclosure of the invention.

BRIEF DESCRIPTION OF THE DRAWINGS

The FIGURE is a process flow diagram showing an alternate arrangement for the process of this invention.

DETAILED DESCRIPTION OF THE INVENTION

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include heterogeneous catalyst such as solid acids and homogenous catalysts, in particular halogenated catalysts such as boron trifluoride as described in U.S. Pat. Nos. 3,906,053, 3,916,019 and 3,981,941.

Preferred catalyst for the oligomerization reaction can generally be described as mild protonic acids. The preferred acids will generally have a Hammett acidity function of 4.0 or a lower acid strength with Hammett acidity values of 5.0 or more being preferred. Examples of catalysts falling into this category include ion exchange resin catalysts, such as sulfonated ion exchange resins, and phosphoric acid catalysts. A particularly preferred catalyst is a solid phosphoric acid (SPA) catalyst which has a Hammett acidity function of 5.0. The SPA catalyst refers to a solid catalyst that contains as a principal ingredient an acid of phosphorus such as ortho-, pyro- or tetraphosphoric acid.

SPA catalyst is normally formed by mixing the acid of phosphorus with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. Nos. 3,050,472; 3,050,473, and 3,132,109 and from other references.

Oligomerization zones in general are maintained at conditions which may vary widely due to the previously listed variables. In this invention the oligomerization reaction zone is preferably operated at temperatures and pressures that increase the compatibility of its effluent conditions with the inlet conditions of the saturation reaction zone inlet and its inlet conditions with the dehydrogenation reaction zone effluent conditions. The preferred temperature of the oligomerization reaction zone may be in a range of from 100 to 500° F., will typically be in a range of from 200 to 500° F. and will more typically be in a range of from 300 to 450° F. Pressures within the oligomerization reaction zone will usually be in a range of from 100 to 1200 psig and more typically in a range of from 200 to 1000 psig. When practicing this invention the preferred operating pressure for the SPA catalyst will be in a range of from 100 to 1000 psig and more typically in a range of from 200 to 1000 psig with pressure of 200 to 500 psig being particularly preferred. Oligomerization conditions may also include a liquid hourly space velocity (LHSV) of 0.5 to 5 $hr^{-1}$. It has also been found that maintaining operating temperatures in a narrow range of from 300 to 400° F. can push selectivity toward the production of more $C_8$ isomers.

The feed to the oligomerization zone reaction will typically comprise $C_3$ to $C_5$ olefins and paraffins, but may comprise olefins having carbon numbers of 12 or higher. Steam or water may be fed into the reactor to maintain a low water content for hydration of the preferred SPA catalyst. The source of the olefin feeds are typically a light gas stream recovered from the gas separation section of an FCC process, $C_4$ streams from steam cracking and coker off gas or the effluent from dehydrogenation zone. The olefin feed stream is characterized by having an overall $C_4$ olefin concentration of at least 10 wt %. In most operations, this olefin feed stream will contain $C_4$ olefins but it may also constitute all or substantial quantities of $C_3$ olefins. Typically the olefin feeds can have a $C_3$ to $C_5$ olefin concentration of at least 30 wt %. The principal oligomerization products comprise $C_8$ and heavier olefins. The principal reaction substrate in the reaction zone will comprise propylene or normal butene. Where $C_3$ olefins are present as feed, these olefins will primarily combine to produce $C_9$ and higher alkenes. Preferred feeds will have a concentration of at least 30 wt % and more preferably at least 50 wt % total olefins in the feed stream. The olefin content of the feed may predominately comprise normal olefins of a single carbon number.

The presence of the heavy paraffins promotes liquid phase conditions in the oligomerization zone. The combined cycloparaffin stream and feed will usually maintain at least partial liquid phase conditions in the oligomerization zone. Partial liquid phase conditions refers to maintaining at least 10 wt % of the combined cycloparaffin stream and feed in liquid phase. Preferably at least 50 wt % of the combined feed and cycloparaffin are in liquid phase in the oligomerization zone to provide substantial liquid phase conditions, and more preferably essentially all, i.e. at least 90 wt %, of the fluid in the oligomerization zone will be in liquid phase.

In the practice of this invention cycloparaffin components contact the catalyst in conjunction with the usual oligomerization zone feed. The cycloparaffin components will have at least 5 carbon atoms and more preferably at least 6 carbon atoms. Cyclic paraffins without pendant side alkyl groups are usually preferred. The cycloparaffins will usually comprise cyclopentane and cyclohexane. Cyclohexane has sufficient vapor pressure to maintain reactor vapor fractions in the 20–60% range when mixed 1/1 with a propane recycle and maintained at typical oligomerization conditions of 550 psia and 340–380° F. Further adjustment in the vapor pressure and liquid volume may be made by adding lighter or heavier cycloparaffins to a cyclohexane base stream.

The effective washing action of the heavy hydrocarbons requires a minimum liquid mass flux. Preferred rates for the liquid mass flux will exceed 3000 $lb/hr/ft^2$. The effectiveness of the liquid mass flux may be improved by the incorporation of a suitable inlet distributor at the top of the reactor. For multi-bed reactors the use of an inlet distributor in the first reactor may be the most critical because of the significant amount of reaction that takes place in that reactor.

The cycloparaffin components may enter the process with the incoming feed or may be injected into an oligomerization reaction zone at intermediate locations within a single catalyst bed or a number of catalyst beds. It is preferred to have the cycloparaffin present as the feed initially enters the reaction zone to maximize the benefit of the cycloparaffin in the process. In such cases it is typical to have at least 40 wt % and more often 50% or more of the total cycloparaffin stream enter the first reactor with the feed. Additional quantities of the cycloparaffin may be injected in stages through process to maintain temperature control throughout the bed or beds of oligomerization catalyst.

Where the oligomerization zone has a multiple bed arrangement, the different catalyst beds are preferably contained within one or more cylindrical, vertically oriented vessels and the feed stream preferably enters the top of the reactor. The catalyst is preferably disposed in fixed beds within the oligomerization zone in what is known as a chamber-type reactor structure. Typically, a chamber-type reactor will contain about five catalyst beds. In a chamber-type reactor, the reactants flow through a series of large diameter catalyst beds. The temperature of the reactants may be further controlled by recycling additional relatively inert hydrocarbons to act as a heat sink. Oligomerization reaction zones are routinely arranged with such multiple beds of catalyst that receive an intermediate injection of a quench material to control temperatures from the exothermic reaction. Substantial advantage can be obtained by adding cycloparaffins as an intermediate injection stream that also benefits the process by serving as a quench stream.

With the addition of the cycloparaffin stream the combined feed to the oligomerization zone will preferably have a ratio of light and cycloparaffin to olefins of from 1:1 to 5:1. Thus, the paraffin concentration of the feed to the oligomerization reaction zone will typically be at least 50 wt % and more typically at least 70 wt %. A high percentage of the olefins in the feed stream are reacted in the oligomerization reaction zone. The olefin conversion will typically range of from 80 to 99 wt %.

The effluent from the oligomerization reaction zone will normally enter a separator. Separation of the effluent stream from the oligomerization zone will at minimum recover the cycloparaffins from the effluent for recycle to the oligomerization zone. The usual separator for recovery of the product oligomers also recovers unreacted feed as an overhead stream and at least a portion of the cycloparaffin stream for recycle to the oligomerization zone. The paraffins for recycle may be recovered with the product stream or the unreacted feed olefins.

Where product recovery limits the bottom capacity of existing fractionation zones, using cycloparaffin with lower carbon numbers than the product oligomers has advantages. Relatively lower carbon number paraffins may be recovered overhead with unreacted feed components for combined recycle back to the oligomerization zone. Where column flooding limits overhead recovery of relatively lighter paraffins, it may be beneficial to recover a recycle paraffin stream as a sidecut.

The recovered cycloparaffin stream will often contain some oligomers that are difficult to separate. For the most part these oligomers will comprise dimers such as hexene. Any separation difficulty for these closely boiling oligomers will not usually pose a problem. In most cases these are effectively recycled with the cycloparaffins to produce more desired heavy oligomer products.

Addition of the cycloparaffins stream will provide a substantial quantity of such paraffins in the oligomerization zone and preferably will produce a minimum of 20 wt % cycloparaffins in the reactor effluent stream and will more typically produce at least 15 wt % of cycloparaffins at the inlet of each catalyst bed in the reaction zone. $C_6$ cycloparaffins are particularly preferred and will preferably comprise at least 10 to 30 wt % of the mass flow through the oligomerization reaction zone. In many cases the weight ratio of heavy saturate to the olefin feed is in a range of from 0.5 to 4 and more often in a range of from 1 to 2.

The ease of separating the cycloparaffins from the effluent stream products minimizes the carryover of heavy olefins into the recycle stream and cycloparaffins into the product. Therefore, after the initial supply of the cycloparaffins for circulation in the recycle stream there should be little need for make-up cycloparaffins for circulation through the process. Some cycloparaffins will inevitably be lost with product oligomers or purposefully purged to maintain a sufficiently low concentration of contaminants in the cycloparaffin recycle.

The source of the cycloparaffins to the oligomerization zone can be any stream that can supply the higher carbon number paraffins in the necessary quantities. The cycloparaffins are usually imported into the process from external sources. Cycloparaffin, in particular cyclohexane is readily available in relatively pure form and at generally low cost. Therefore sources for the initial supply of such cycloparaffins and any required make-up will be abundant in most operation locations.

In most cases the cycloparaffins will have an at least a two carbon number difference between the paraffin stream and the product oligomers which simplifies separation and recovery of the paraffin recycle. For example where the product oligomers comprise $C_9$ oligomers the heavy saturate stream will comprise $C_7$-or cycloparaffins.

The process and different operational steps will be described in conjunction with the FIGURE. The FIGURE shows only a limited form of the invention and only those portions of the process that are necessary to gain an understanding of the invention and the necessary means of integrating the principal processing steps that comprise the invention. Further details related to valves, control means, pumps, compressors, coolers, and other necessary processing equipment are well known to those skilled in the art and not described in detail unless necessary for an understanding of the invention.

In the arrangement of the FIGURE an oligomerization zone feed stream, containing 70 to 90 wt % propylene is brought into the process by a line 30 and combined with a recycle stream containing cyclohexane by a line 32. A line 34 carries the combined feed and recycle paraffin stream into optional combination with light olefins and paraffins from a line 31. An exchanger 33 heats the feed against a stream 35 of flashed vapors from the overhead of a flash drum 39. A line 36 passes the combined feed through a heater 37 and an effluent exchanger 38 to raise the combined feed to its initial reaction temperature. The combined feed, including the cyclohexane, enters a multi-bed reactor 41 at a temperature of 320° F. and a pressure of 550 psia for contacts with a SPA catalyst. A line 42 carries flashed overhead vapor through a condenser 43. The overhead stream will usually comprise $C_3$ and lighter hydrocarbons including unreacted feed olefins and light paraffins. Condenser 43 prepares the flash overhead for introduction as a quench into one or more of the catalyst beds of reactor 41. A line 45 introduces the quench into reactor 41 together with any optional addition of cycloparaffin from a line 44.

Line 40 delivers the oligomerization effluent at temperature of 360° F. for heat and product recovery. The effluent contains unreacted feed olefins, light and cycloparaffins, and oligomers. After cooling against the incoming feed in exchanger 38, the mixed contents of line 40 enter flash drum 39 in mixed phase. Flash drum 39 produces an overhead stream rich in $C_3$ olefins and lower boiling hydrocarbons that is recycled to reactor 41 as previously described. Line 46 carries bottoms liquid containing absorbed light hydrocarbons to a fractionation zone for removal of a net propane stream via a line 48. Bottoms from fractionator 48 enter a fractionator 50. Fractionator 50 maintains a cut point between lighter hydrocarbons and the cyclohexane recycle by withdrawing an overhead 51 comprising mainly $C_4$ hydrocarbons and a sidecut stream 52. Sidecut stream 52 comprising mainly cyclohexane for recycle to the reaction zone as previously described. Sidecut stream 52 may also contain $C_6$ olefins that undergo further combination to produce more product oligomers. The remaining heavier fraction of the effluent consists mainly of heavier trimers and tetramers that pass to fractionator 54. Fractionator 54 recovers the $C_9$ trimers overhead via line 55 while $C_{12}$ tetramers and higher oligomers leave the process through bottom stream 56.

What is claimed is:

1. An oligomerization process for the production of $C_8$ and higher carbon number olefins, said process comprising:

a) passing an oligomerization zone feed comprising $C_3$ and/or higher carbon number olefins to an oligomerization zone and contacting the oligomerization zone feed at oligomerization conditions with an oligomerization catalyst;

b) passing a saturate stream comprising cycloparaffins having a carbon number of at least 5 into contact with said feed and said catalyst;

c) recovering an oligomerization effluent stream comprising said paraffins and product oligomers having 8 or more carbon atoms.

2. The process of claim 1 wherein the oligomerization conditions include a temperature of 200 to 500 F.°, a pressure of 100 to 1000 psig, and an LHSV of 0.5 to 5.

3. The process of claim 1 wherein said oligomerization zone operates at a temperature in a range of from 300 to 450° F.

4. The process of claim 1 wherein said oligomerization effluent stream is passed to a separator and separated into a product stream comprising $C_8$ or higher carbon number olefins and into said cycloparaffin stream, at least a portion of said cycloparaffin stream is recycled to said oligomerization zone, and a cycloparaffin make-up stream is combined with said oligomerization zone feed to replace lost cycloparaffins.

5. The process of claim 1 wherein at least a portion of said cycloparaffin stream enters said oligomerization zone with the feed.

6. The process of claim 1 wherein at least 50 wt % of the product olefins comprise hydrocarbons having carbon numbers at least two carbon numbers higher than at least 50 wt % of the carbon number of the cycloparaffin stream.

7. The process of claim 1 wherein the weight ratio of the cycloparaffin to olefin feed is in a range of from 0.5 to 2.

8. The process of claim 7 wherein at least 40 wt % of the cycloparaffin stream enters the oligomerization zone with the incoming feed.

9. The process of claim 1 wherein the product oligomers comprise $C_8$ or higher carbon number oligomers and the cycloparaffin stream comprises cyclohexane.

10. The process of claim 1 wherein said oligomerization zone catalyst comprises a solid phosphoric acid catalyst.

11. The process of claim 1 wherein the saturate stream comprises $C_5$ to $C_7$ cycloparaffins.

12. An oligomerization process for the production of $C_9$ and higher carbon number oligomers, said process comprising:

a) passing an oligomerization zone feed comprising $C_3$ and/or $C_4$ olefins to an oligomerization zone and contacting the oligomerization zone feed at oligomerization conditions with a solid phosphoric acid catalyst;

b) passing cyclohexane containing stream into contact with said feed and said catalyst in the oligomerization zone to maintain at least a portion of the combined cyclohexane stream and feed in liquid phase conditions in the oligomerization zone;

c) recovering an oligomerization effluent stream comprising said cyclohexane and product oligomers comprising $C_9$ and higher olefin products; and, d) separating said oligomerization effluent stream to produce an oligomerization product stream comprising product oligomers and to recover at least a portion of said cyclohexane.

13. The process of claim 12 wherein the oligomerization product stream contains less than 10 to 20 wt % of $C_8$ and lower carbon number hydrocarbons.

14. The process of claim 13 wherein cyclohexane is recovered as a sidecut stream from a separator.

15. The process of claim 14 wherein the sidecut stream contains $C_6$ olefins.

16. The process of claim 12 wherein the oligomerization conditions include a temperature of 200 to 500 F.°, a pressure of 100 to 1000 psig, and an LHSV of 0.5 to 5.

17. The process of claim 12 wherein the oligomerization zone is maintained in a substantial liquid phase.

18. The process of claim 17 wherein at least 50 wt % of the oligomerization effluent exits the oligomerization zone in liquid phase.

19. The process of claim 12 wherein at least a portion of said heavy saturate stream enters said oligomerization zone with the feed.

20. The process of claim 12 wherein the weight ratio cyclohexane to olefin feed is in a range of from 1 to 2.

* * * * *